United States Patent [19]
Hofmann

[11] Patent Number: 5,318,514
[45] Date of Patent: Jun. 7, 1994

[54] APPLICATOR FOR THE ELECTROPORATION OF DRUGS AND GENES INTO SURFACE CELLS

[75] Inventor: Gunter A. Hofmann, San Diego, Calif.

[73] Assignee: BTX, Inc., San Diego, Calif.

[21] Appl. No.: 931,061

[22] Filed: Aug. 17, 1992

[51] Int. Cl.⁵ ............................................. A61N 1/30
[52] U.S. Cl. ........................................ 604/20; 607/145; 607/150
[58] Field of Search ............... 604/20; 128/783, 800, 128/802, 803, 801, 784; 607/116, 145, 149, 150, 151, 153, 115

[56] References Cited

U.S. PATENT DOCUMENTS

| | | | |
|---|---|---|---|
| 4,033,356 | 7/1977 | Hara | 128/801 X |
| 4,090,517 | 5/1978 | Takenaka | 604/20 X |
| 4,180,079 | 12/1979 | Wing | 128/803 X |
| 4,689,039 | 8/1987 | Masaki | 604/20 |
| 4,837,049 | 6/1989 | Byers et al. | 128/642 X |
| 4,942,883 | 7/1990 | Newman | 604/20 X |
| 4,953,565 | 9/1990 | Tachibana et al. | 604/20 |
| 4,997,418 | 3/1991 | DeMartini | 604/20 |
| 5,002,527 | 3/1991 | Reller et al. | 604/20 |
| 5,012,816 | 5/1991 | Lederer | 128/800 X |
| 5,019,034 | 5/1991 | Weaver et al. | 604/20 |
| 5,037,381 | 8/1991 | Bock et al. | 604/20 |
| 5,084,008 | 1/1992 | Phipps | 604/20 |
| 5,156,591 | 10/1992 | Gross et al. | 604/20 |
| 5,160,316 | 11/1992 | Henley | 128/803 X |
| 5,162,042 | 11/1992 | Gyory et al. | 128/802 X |
| 5,162,043 | 11/1992 | Lew et al. | 128/802 X |

FOREIGN PATENT DOCUMENTS 1291101  2/1987  U.S.S.R. ............................. 128/800

Primary Examiner—Lee S. Cohen
Assistant Examiner—Samuel Gilbert
Attorney, Agent, or Firm—Baker, Maxham, Jester & Meador

[57] ABSTRACT

An apparatus for implanting macromolecules such as genes, DNA or pharmaceuticals into a preselected surface tissue region of of a patient. An applicator having a plurality of electrodes is provided for contacting a surface tissue region of a patient. A mechanism associated with the applicator delivers a predetermined quantity of a fluid medium carrying the preselected macromolecules. A signal generator is provided for generating a predetermined electric signal. The electrodes of the applicator are connected to the signal generator for applying an electric field in the surface tissue region. The field has a predetermined strength and duration in order to make the walls of a plurality of cells in the surface tissue region transiently permeable to permit the macromolecules to enter said preselected cells without damaging said cells. This enhances the uptake of macromolecules and thus enhances the therapeutic effect achieved.

20 Claims, 1 Drawing Sheet

APPLICATOR FOR THE ELECTROPORATION OF DRUGS AND GENES INTO SURFACE CELLS

BACKGROUND OF THE INVENTION

The present invention relates to the treatment of ailments in humans and other mammals, and more particularly, to apparatus for delivering pharmaceutical compounds and genes into live cells of a patient.

Somatic cell gene therapy is being pursued in many laboratories. It is known that DNA can be directly injected into certain tissues to cause production of the protein it encodes. This technique may allow physicians to treat human diseases with therapeutic genes. The injected genes may cause the tissues to produce the desired proteins for as long as several months. Most of the current research is focused on the use of marrow stem cells. However, another tissue being considered as a vehicle for gene therapy is the epidermis which is composed mainly of keratinocytes. These cells primarily serve a protective function. However, there is evidence that they may secrete a variety of cytokines and growth factors. See "Prospects for Epithelial Gene Therapy, in: DNA Damage and Repair in Human Tissues", Edited by Sutherland and Woodhead, Plenum Press, New York, 1990, pages 215–223. It appears possible to utilize genetically transformed epithelial cells to treat diseases in distant sites in the body.

U.S. Pat. No. 5,019,034 of Weaver et al. entitled CONTROL OF TRANSPORT OF MOLECULES ACROSS TISSUE USING ELECTROPORATION discloses a method of transporting molecules across tissue which comprises the steps of applying at least one electrical pulse in order to cause electroporation in a region and utilizing a driving force to move molecules across the region. In the specification "driving force" is defined as including iontopheresis, pressure gradients and concentration gradients. The Weaver et al. patent also discloses a method of temporarily increasing the permeability of tissue which comprises applying at least one electrical pulse of sufficient voltage and duration to a region of tissue to cause a reversible electrical breakdown in an electroporated region and wherein the electroporated region is used as a site of molecular transport. The examples given in the Weaver et al. patent all appear to deal with enhanced permeability of samples of skin. Weaver et al. provides only a diagrammatic illustration of an apparatus comprising three inverted U-shaped electrodes 16 in contact with the surface of tissue 22.

SUMMARY OF THE INVENTION

Accordingly, it is the primary object of the present invention to provide an apparatus that will permit therapy through the insertion of genes into surface cells.

The present invention provides an apparatus for implanting macromolecules such as genes, DNA or pharmaceuticals into a preselected surface tissue region of of a patient. An applicator having a plurality of electrodes is provided for contacting a surface tissue region of a patient. A mechanism associated with the applicator delivers a predetermined quantity of a fluid medium carrying the preselected macromolecules. A signal generator is provided for generating a predetermined electric signal. The electrodes of the applicator are connected to the signal generator for applying an electric field in the surface tissue region. The field has a predetermined strength and duration in order to make the walls of a plurality of cells in the surface tissue region transiently permeable to permit the macromolecules to enter said preselected cells without damaging said cells. This enhances the uptake of macromolecules and thus enhances the therapeutic effect achieved.

BRIEF DESCRIPTION OF THE DRAWINGS

Throughout the drawing figures, like reference numerals refer to like parts.

DESCRIPTION OF THE PREFERRED EMBODIMENTS

The present invention takes advantage of the phenomenon known as electroporation in order to improve the uptake of genes, DNA and/or pharceuticals, hereinafter "macromolecules", into surface tissues of humans and other living organisms. Electroporation involves the transient formation of pores in cell membranes utilizing short pulses of high voltage electric fields. DNA and other macromolecules can enter the cells after pores are formed in the cell walls. Thereafter they stay encapsulated in the cells and the cell walls reseal themselves. The DNA can combine with the genome of the cells and alter their genetic properties.

Figure 1:
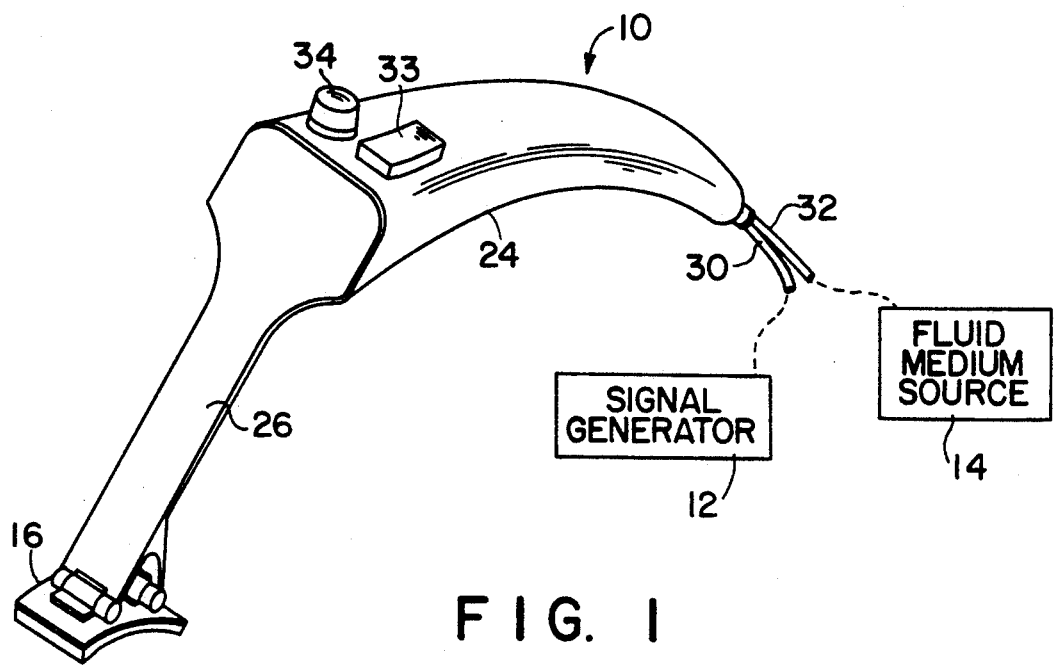
FIG. 1 is a perspective view of a first embodiment of my apparatus for electroporation of drugs or genes into surface cells.

Referring to FIG. 1, a first embodiment of the apparatus of the present invention comprises a manually positionable applicator 10 which is connected to a signal generator 12 and a fluid medium source 14. The applicator 10 has a head assembly 16 which engages a preselected surface tissue region of a patient.

Figure 2:
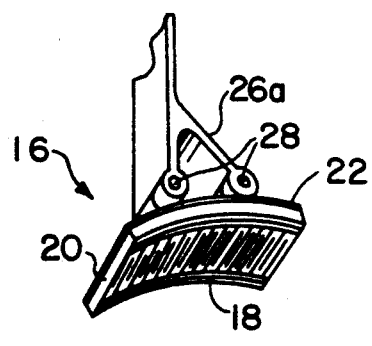
FIG. 2 is an enlarged view of the head assembly of the first embodiment.

Details of the head assembly 16 are illustrated in FIG. 2. It comprises a serpentine conductor 18 which is carried on an open pore foam elastomer 20 carried by a flexible, semi-rigid or firm dielectric planar support member 22. Adjacent parallel segments of the conductor 18 serve as electrodes.

The applicator 10 (FIG. 1) further includes a handle portion 24 and an arm portion 26. The head assembly 16 is connected to a Y-shaped distal end 26a (FIG. 2) of the arm portion 26 via pins 28.

The terminal ends of the conductor 18 are connected to the signal generator 12 via cable 30. A fluid medium carrying the macromolecules is contained within the fluid medium source 14 which may include a motorized pump or pressure source. The fluid medium source 14 is coupled to the foam elastomer 20 by a flexible tube 32 which extends through the applicator 10. An actuator button 33 on the handle portion 24 of the applicator may be depressed to deliver a suitable quantity of the fluid medium to the foam elastomer 24. The elastomer 20 provides a sponge-like substrata for holding a predetermined quantity of the fluid medium.

The head assembly 16 is placed in contact with the preselected surface tissue region of the patient, i.e. the skin on the forearm or the surface of an organ. This places the conductor 18 in contact with the skin. Fluid medium carrying the macromolecules is also transferred to the skin as a result of the compression of the soaked elastomer 20. A pushbutton switch 34 on the handle portion 24 is then depressed to deliver a high voltage pulse to the conductor 18. The resulting electric field is contained between the adjacent parallel segments of the electrode 18 and into a depth of the skin proportional to the gap between these segments. The electric filed is effective to inject the fluid into the tissue region. The fluid medium from the elastomer 20 is physically located between the parallel segments of the conductor 18 which act as electrodes.

The signal generator 12 is energized when the pushbutton 34 is depressed. The function of the signal generator 12 is to generate a predetermined electric signal which, when applied to the conductor 18, results in applying electric fields of a predetermined strength and duration to the preselected surface tissue region. Preferably these fields are applied repeatedly and their strength and duration make the walls of the epithelial cells in the preselected surface tissue region sufficiently permeable to permit the macromolecules to enter the cells without damaging or killing them.

Figure 3:
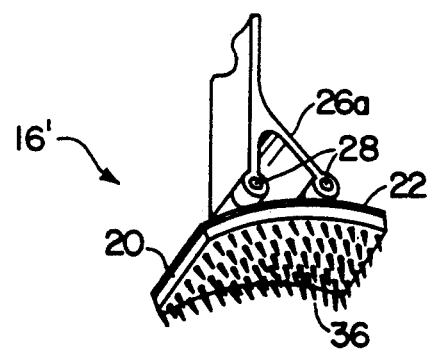
FIG. 3 is an enlarged view of the head assembly of a second embodiment.

It may be necessary to remove the top layer of mostly dead skin cells in order to electroporate the macromolecules into viable skin cells. FIG. 3 illustrates an alternate embodiment of the head assembly 16' which includes a plurality of fine needles 36 extending generally perpendicular to the planar support 22. The needles are arranged in rows and are alternately connected to the output of the signal generator 12 so that each needle is adjacent another of opposite polarity. This may be accomplished utilizing a suitable connector frame or bus (not illustrated). The needles penetrate the outermost layers of the dead skin cells and facilitate the electroporation of the macromolecules into live epithelial cells.

One suitable signal generator is the ELECTRO CELL MANIPULATOR Model ECM 600R commercially available from BTX, Inc. of San Diego, Calif., U.S.A. The ECM 600 signal generator generates a pulse from the complete discharge of a capacitor which results in an exponentially decaying waveform. The electric signal generated by the ECM 600R signal generator is characterized by a fast rise time and an exponential tail.

A number of variables are considered in achieving a desired pulse length with the ECM 600R signal generator. These include the type of fluid medium, voltage and timing mode, and volume. In the ECM 600R signal generator, the electroporation pulse length is set by selecting one of ten timing resistors marked R1 through R10. They are active in both High VM (capacitance fixed at fifty microfarads) and Low VM (with a capacitance range from 25 to 3,175 microfarads.

The passage of an electrical current across the cell membrane results in the creation of transient pores which are critical to the electroportion process. The ECM 600R signal generator provides the voltage (in kV) that travels across the chamber gap (in cm) between the electrodes. This potential difference defines what is called the electric field strength where E equals kV/cm. Each cell species has its own critical field strength for optimum electroportion. This is due to cell size, membrane make-up and individual characteristics of the cell wall itself. For example, some Gram positive bacteria are quite resistant to electroporation and require very high field strengths, i.e., greater than 17 kV (cm), before cell death and/or electroporation occurs. Generally, the required field strength varies inversely to the size of the cell.

The ECM 600R signal generator has a knob that permits the adjustment of the amplitude of the set charging voltage applied to the internal capacitors from 50 to 500 volts in low VM and from 0.05 to 2.5 kV in the High VM. The amplitude of the electrical signal is shown on a display incorporated into the ECM 600R signal generator. This device further includes a plurality of push button switches for controlling pulse length, in the LOW VM mode, by a simultaneous combination of resistors parallel to the output and a bank of seven selectable additive capacitors.

The ECM 600R signal generator also includes a single automatic charge and pulse push button. This button may be depressed to initiate both charging of the internal capacitors to set the voltage and to deliver a pulse to the flow-through chamber in an automatic cycle that takes less than five seconds. The manual button may be sequentially pressed to repeatedly apply the predetermined electric field to the tissues adjacent the needles. Alternatively, a repetitive charge/pulse mode may be selected with an adjustable repetition rate. In this particular application of the ECM 600R, the pushbutton switch 34 on the handle portion 24 of the applicator 10 is connected to the signal generator so as to function in place of its normal panel-mounted push button.

The waveforms of the electrical signal provided by the signal generator 12 can be an exponentially decaying pulse, a square pulse, a uni-polar oscillating pulse train or a bipolar oscillating pulse train. The electric field strength can be 0.2 kV cm to 20 kV/cm. The pulse length can be ten microseconds to one hundred milliseconds. By way of example, there can be one to one hundred consecutive pulses. Of course the waveform, electric field strength and pulse duration are dependent upon the type of cells and the type of macromolecules that are to enter the cells via electroporation.

While I have described two preferred embodiments of my applicator for the electroporation of drugs and genes into surface cells, it should be understood that modifications and adaptations thereof will occur to persons skilled in the art without departing from the spirit of my invention. Therefore, the protection afforded my invention should only be limited in accordance with the scope of the following claims.

I claim:

1. An apparatus for enabling the electroporation of macromolecules into cells of a preselected surface tissue region of a patient, comprising:

an applicator including a handle portion and a head assembly and means for connecting to a source of a fluid medium, the head assembly having means for transferring a predetermined quantity of the fluid medium carrying preselected macromolecules onto said preselected surface tissue region of said patient;

means for generating a predetermined electric signal in the form of a pulse train having a field strength from about 0.2 kV/cm to about 20 kV/cm, and pulse length of form about ten microseconds to about one hundred microseconds;

electrode means carried by said head assembly and connected to the signal generating means and responsive to said electrical signal for applying an electric field in the form of a pulse train of a predetermined strength from about 02. kV/cm to about 20 kV/cm, and duration of from about ten microseconds to about one hundred microseconds in said surface tissue region in order to make walls of a plurality of cells in the surface tissue region transiently permeable to permit said macromolecules to enter said cells; and, control means on said handle portion for controlling communication of said electrical signal form said signal generating means to said electrode means.

2. An apparatus according to claim 1 wherein the means for transferring the quantity of fluid medium carrying the macromolecules includes an open pore foam elastomer mounted in the head assembly.

3. An apparatus according to claim 1 wherein the electrode means includes a serpentine conductor.

4. An apparatus according to claim 1 wherein the head assembly includes a flexible, but firm dielectric planar support.

5. An apparatus according to claim 1 wherein the electrode means comprises a plurality of needles.

6. An apparatus according to claim 1 wherein the applicator includes an arm portion connecting the head assembly with the handle portion.

7. An apparatus according to claim 6 wherein the handle portion includes a pushbutton switch for energizing the signal generating means.

8. An apparatus according to claim 1 and further comprising a source of the fluid medium communicating with said applicator.

9. An apparatus according to claim 6 wherein the arm portion has a Y-shaped terminal end connected to the head assembly.

10. An apparatus for enabling the electroporation of macromolecules into the cells of a preselected surface tissue region of a patient, comprising;

a source of fluid medium;

an applicator including a handle portion and a head assembly having means for transferring a predetermined quantity of said fluid medium carrying preselected macromolecules onto a preselected surface tissue region of a patient;

means for generating a predetermined electric signal; and electrode means carried by the head assembly and connected to the signal generating means for applying an electric field of a predetermined strength and duration in the surface tissue region in order to make the walls of a plurality of cells in the surface tissue region transiently permeable to permit the macromolecules to enter said preselected cells without damaging said cells wherein the handle portion includes a pushbutton means for causing the source of fluid medium to deliver the predetermined quantity of fluid medium to the had assembly.

11. An apparatus according to claim 9 wherein the means for transferring the quantity of fluid medium carrying the macromolecules includes an open pore foam elastomer mounted in the head assembly.

12. An apparatus according to claim 9 wherein the electrode means includes a serpentine conductor.

13. An apparatus according to claim 9 wherein the electrode means comprises a plurality of needles.

14. An apparatus according to claim 9 wherein the head assembly includes a flexible, but firm dielectric planar support.

15. An apparatus according to claim 14 wherein the applicator includes an arm portion connecting the head assembly with the handle portion.

16. An apparatus for enabling the electroporation of macromolecules into the cells of a preselected surface tissue region of a patient, comprising:

a source of fluid medium;

a hand manipulable applicator having a handle portion and a head assembly having means for transferring a predetermined quantity of said fluid medium carrying preselected macromolecules onto a preselected surface tissue region of a patient;

means for generating a predetermined electric signal; and electrode means carried by the head assembly for contact with said preselected surface tissue; and and control means on said handle portion for enabling said source of the fluid medium for delivery of said predetermined quantity of fluid medium to said head assembly and for enabling the signal generating means for delivery of said predetermined electric signal to the electrode means for applying an electric field in the form of a pulse train of a predetermined strength from about 0.2 kV/cm to about 20 kv/cm, and pulse duration of from about ten microseconds to about one hundred milliseconds in the surface tissue region in order to make the walls of a plurality of cells in the surface tissue region transiently permeable for enabling the macromolecules to enter said preselected cells without damaging said cells.

17. An apparatus according to claim 16 wherein the means for transferring the quantity of fluid medium carrying the macromolecules includes an open pore foam elastomer mounted on the head assembly.

18. An apparatus according to claim 17 wherein the head assembly includes a flexible, but firm dielectric planar support.

19. An apparatus according to claim 18 wherein the electrode means comprises a plurality of needles.

20. An apparatus according to claim 18 wherein the electrode means comprises a serpentine conductor.

* * * * *